US012031950B2

(12) United States Patent
Kemp et al.

(10) Patent No.: US 12,031,950 B2
(45) Date of Patent: Jul. 9, 2024

(54) ULTRASONIC SENSOR FOR GUIDED WAVE TESTING

(71) Applicant: Guided Ultrasonics Ltd, Brentford (GB)

(72) Inventors: Nick Kemp, Brentford (GB); Keith Vine, Brentford (GB)

(73) Assignee: Guided Ultrasonics Ltd, London (GB)

(*) Notice: Subject to any disclaimer, the term of this patent is extended or adjusted under 35 U.S.C. 154(b) by 287 days.

(21) Appl. No.: 17/601,671

(22) PCT Filed: Mar. 23, 2020

(86) PCT No.: PCT/GB2020/050771
§ 371 (c)(1),
(2) Date: Oct. 5, 2021

(87) PCT Pub. No.: WO2020/201713
PCT Pub. Date: Oct. 8, 2020

(65) Prior Publication Data
US 2022/0163487 A1 May 26, 2022

(30) Foreign Application Priority Data
Apr. 5, 2019 (GB) ..................................... 1904880

(51) Int. Cl.
*G01N 29/04* (2006.01)
*G01N 29/22* (2006.01)
(Continued)

(52) U.S. Cl.
CPC ........... *G01N 29/245* (2013.01); *G01N 29/04* (2013.01); *G01N 29/223* (2013.01);
(Continued)

(58) Field of Classification Search
CPC ........ G01N 29/00; G01N 29/04; G01N 29/22; G01N 29/223; G01N 29/24; G01N 29/245;
(Continued)

(56) References Cited

U.S. PATENT DOCUMENTS 9,404,896 B2 * 8/2016 Kleinert ................. G01N 29/22
2008/0236286 A1 * 10/2008 Lam .................... G01N 29/2437
73/618
(Continued)

FOREIGN PATENT DOCUMENTS

CN 103376230 A 10/2013
EP 2657695 A2 * 10/2013 ......... G01N 27/9093
(Continued)

OTHER PUBLICATIONS

United Kingdom Search and Examination Report for Application No. GB1904880.0, dated Aug. 7, 2019, 5 pages.
(Continued)

*Primary Examiner* — Nguyen Q. Ha
(74) *Attorney, Agent, or Firm* — McCarter & English, LLP; David R. Burns (57) ABSTRACT

An ultrasonic sensor for guided wave testing is disclosed. The sensor comprises a flexible circuit board, an array of piezoelectric elements on the flexible circuit board and an array of permanent magnets. Each piezoelectric element is interposed between a respective permanent magnet and the flexible circuit board.

18 Claims, 9 Drawing Sheets

(51) Int. Cl.
*G01N 29/24* (2006.01)
*G01N 33/204* (2019.01)

(52) U.S. Cl.
CPC ... *G01N 33/204* (2019.01); *G01N 2291/0234* (2013.01); *G01N 2291/106* (2013.01); *G01N 2291/2634* (2013.01)

(58) Field of Classification Search
CPC ............... G01N 33/00; G01N 33/204; G01N 2291/0234; G01N 2291/106; G01N 2291/2634
See application file for complete search history.

(56) References Cited

U.S. PATENT DOCUMENTS

| | | |
|---|---|---|
| 2012/0103097 A1 | 5/2012 | Lopez Jauregui |
| 2017/0038340 A1 | 2/2017 | Galvagni et al. |
| 2020/0240937 A1* | 7/2020 | Landy .................. G01N 29/04 |

FOREIGN PATENT DOCUMENTS

| | | | | |
|---|---|---|---|---|
| GB | 2482300 A | 2/2012 | | |
| GB | 2524991 A | 10/2015 | | |
| JP | 2001174444 A | 6/2001 | | |
| JP | 2008151599 A | * 7/2008 | ............. | G01N 29/24 |
| JP | 2013-231718 A | 11/2013 | | |
| WO | 2013/063676 A1 | 5/2013 | | |
| WO | 2020/201713 A1 | 10/2020 | | |

OTHER PUBLICATIONS

International Search Report and Written Opinion for Application No. PCT/GB2020/050771, dated Jun. 8, 2020, 12 pages.
International Preliminary Report on Patentability for Application No. PCT/GB2020/050771, dated Oct. 14, 2021, 8 pages.

* cited by examiner

ULTRASONIC SENSOR FOR GUIDED WAVE TESTING

CROSS-REFERENCE TO RELATED APPLICATIONS

This application is a 35 U.S.C. § 371 national stage filing of International Application No. PCT/GB2020/050771, filed on Mar. 23, 2020, which claims priority to United Kingdom Patent Application No. 1904880.0, filed on Apr. 5, 2019. The entire contents of each of the aforementioned applications are incorporated herein by reference.

FIELD

The present invention relates to an ultrasonic sensor for guided wave testing of structures, such as pipes.

BACKGROUND

Guided Ultrasonics Ltd (London, UK) currently markets a permanently-installable monitoring system (gPIMS) sensor. The sensor has two rows of piezoelectric elements mounted on a flexible circuit board and two circumferential steel bands which help to hold the sensor in place and provide an electrical earth connection to electrodes on the back of the piezoelectric elements. Although the steel bands help to secure the sensor, the sensor is bonded to the pipe using an epoxy adhesive.

After wiring of a sensor is complete, the assembly is overmoulded with a polyurethane elastomer to provide mechanical and environmental protection, as well as damping for unwanted vibrations that can introduce noise into the received signals. To install the circuit onto a pipe, adhesive is applied to the inside face of the sensor, then the steel bands are tensioned using two spring-loaded bolts. The force on the transducer elements depends on the tension in the bands and is controlled by carefully monitoring the torque applied to the closing bolts.

The piezoelectric elements are divided into groups or "channels" around the circumference of the pipe, typically between six and twelve channels per row. The circumference of a pipe may be such that it may require multiple flexible circuit boards to be used and the number of channels per circuit may need to be adjusted to make allowance for this. For example, if four flexible circuit boards are needed to go around the circumference of a pipe to create a 16-channel ring, then each circuit board will need two rows of elements and two channels per row. Thus, when four circuit boards are combined, there are two rows with eight channels per row.

To test a pipe, an oscillating voltage is sequentially applied to the channels of the array. This causes the transducers to generate shear waves in the pipe. After the transducers have transmitted a signal, they are used to receive reflected vibrations in the pipe and convert them back into electrical signals that can be processed and analysed.

SUMMARY

According to a first aspect of the present invention there is provided an ultrasonic sensor for guided wave testing. The sensor comprises a flexible circuit board, an array of piezoelectric elements on the flexible circuit board and an array of permanent magnets, each piezoelectric element interposed between a respective permanent magnet and the flexible circuit board.

The piezoelectric elements are preferably shear-polarized piezoelectric elements. However, the piezoelectric elements may be thickness polarised, e.g., for guided wave testing of rails. The piezoelectric elements are preferably disposed or supported directly on the flexible circuit board.

The piezoelectric elements may be arranged in first and second rows in a first direction across flexible circuit board. Polarization of the piezoelectric elements in the first row and polarization of the piezoelectric elements in the second row are preferably the same. For example, the polarization of the piezoelectric elements in the first row and the polarization of the piezoelectric elements in the second row are antiparallel. There may be more than two rows, for example, three, four, five or more rows, of piezoelectric elements.

The array of piezoelectric elements may comprise between 10 and 500 piezoelectric elements.

The piezoelectric elements may comprise blocks of lead zirconate titanate (PZT). Each piezoelectric element may be generally a rectangular cuboid. Each piezoelectric element has an orientation-identifying feature, such as a chamfered corner.

The flexible circuit board may comprise a plastics material, such as polyimide, PEEK or polyester. The flexible circuit board may support conductive tracks, for example, copper tracks.

The permanent magnets may comprise ferrite or a rare earth metal, such as neodymium iron boride (NdFeB) or samarium cobalt (SmCo). The permanent magnets may be cuboid. Each permanent magnet may have a notch for accommodating a respective piezoelectric element for reducing a gap between the permanent magnet and the flexible circuit board.

The ultrasonic sensor may further comprise at least one conductive strip running over a line of permanent magnets and on the flexible sheet between the permanent magnets along the sheet. The at least one conductive strip may comprise at least one metallic strip, for example, formed from copper.

The ultrasonic sensor may further comprise a set of wires, wherein each wire is connected to a respective piezoelectric element or to a respective conductive track of the flexible circuit board and the conductive track is connected to one or more respective piezoelectric elements or to a set of at least two piezoelectric elements.

The ultrasonic sensor may further comprise an overmould encapsulating at least the flexible circuit board, the piezoelectric elements, and the permanent magnets.

According to a second aspect of the present invention there is provided a transducer array ring comprising a plurality of ultrasonic sensors of the first aspect.

The transducer array ring may further comprise first and second joining strips arranged to overlap first and second ultrasonic sensors arranged end-to-end and secured to the first and second ultrasonic sensors.

According to a third aspect of the present invention there is provided a method of using the ultrasonic sensor of the first aspect or the transducer array ring of the second aspect, the method comprising attaching the ultrasonic sensor or transducer array ring to a ferromagnetic structure (such as a pipe, wind turbine tower, lamp post or building support).

The ultrasonic sensor or transducer array ring may be secured to the ferromagnetic structure without an adhesive or a retaining band. The ultrasonic sensor or transducer array ring may be secured to the ferromagnetic structure with an adhesive or a retaining band.

The method may further allow removing the attached ultrasonic sensor or transducer array ring from the ferromagnetic structure.

The method may further comprise using the ultrasonic sensor or transducer array ring in or in the vicinity of water.

The method may further comprise installing the ultrasonic sensor or transducer array ring to an inner wall of ferromagnetic structure.

BRIEF DESCRIPTION OF THE DRAWINGS

Certain embodiments of the present invention will now be described, by way of example, with reference to the accompanying drawings, in which.

DETAILED DESCRIPTION

Figure 1:
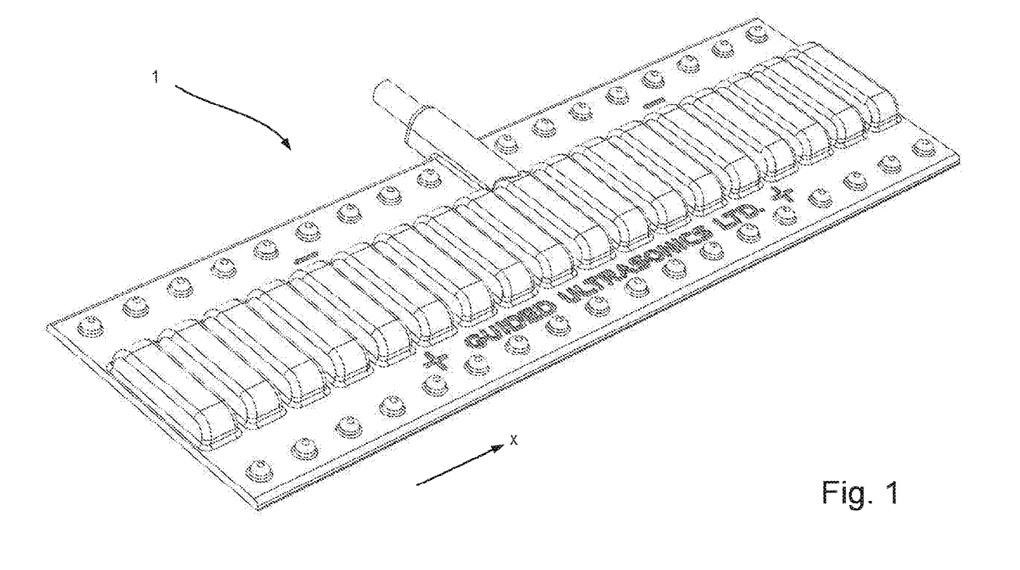
FIG. 1 is a perspective view of an ultrasonic sensor strip comprising an overmould.
Figure 2:
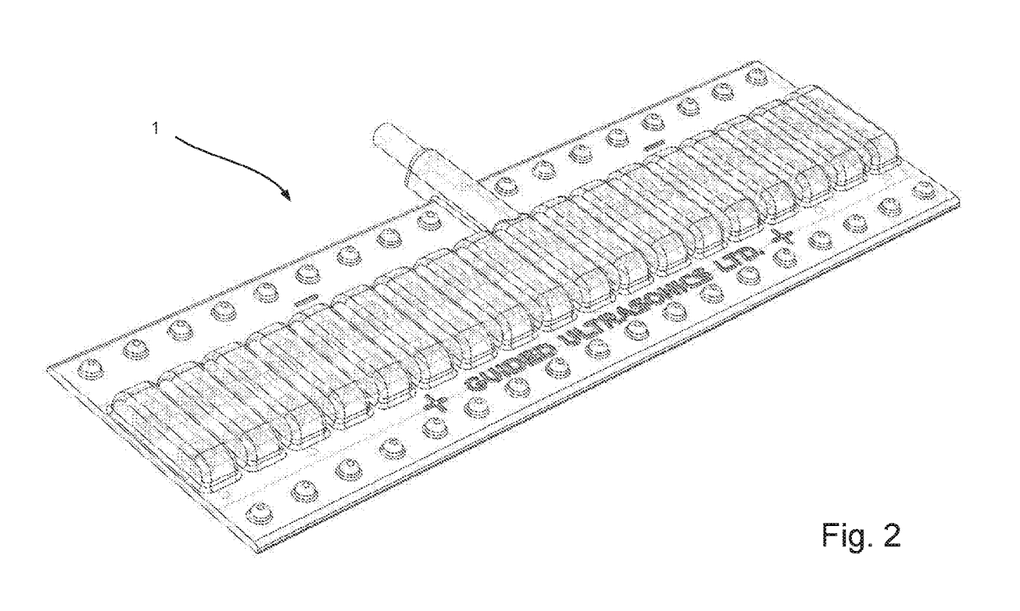
FIG. 2 is another perspective view of the ultrasonic sensor strip shown in FIG. 1 with the overmould shown semi-transparent for clarity to illustrate other parts of the sensor strip.
Figure 3:
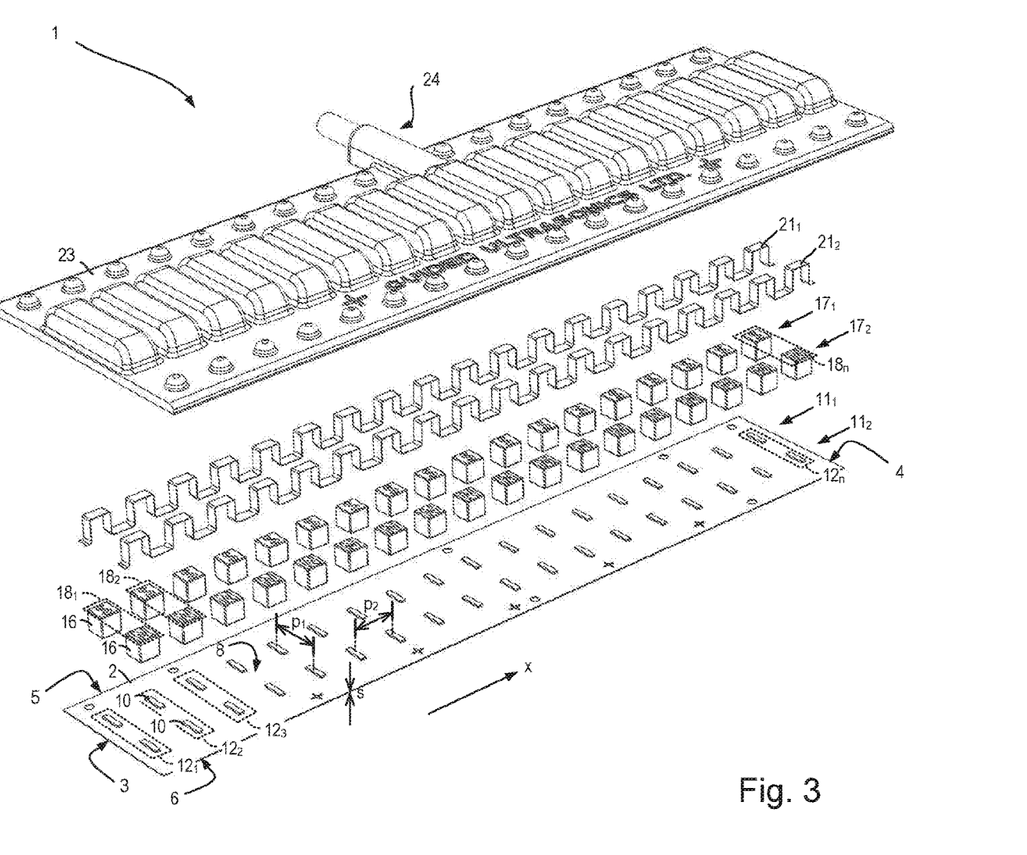
FIG. 3 is an exploded view of the ultrasonic sensor strip shown in FIG. 1.

Referring to FIGS. 1 to 3, an ultrasonic sensor strip 1 for use in guided wave testing of a structure, such as a pipe, is shown. As will be explained in more detail hereinafter, two or more ultrasonic sensor strips 1 may be joined together to form a transducer array ring 31 (FIG. 11) for inspecting a larger structure, such as a large-diameter pipe. The sensor strip 1 and transducer ring can be secured without the use of an adhesive or a tensioning band to a structure made from a ferromagnetic material, such as steel.

Figure 9:
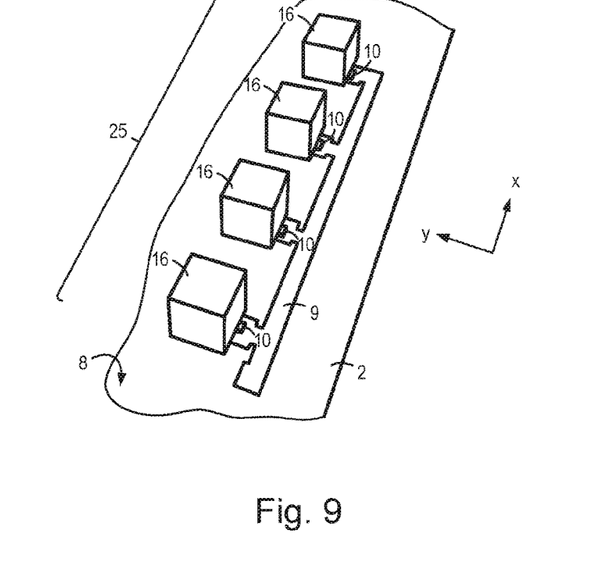
FIG. 9 is a perspective view of part of flexible circuit board, piezoelectric transducers, an array of permanent magnets and conductive tracks.
Figure 10:
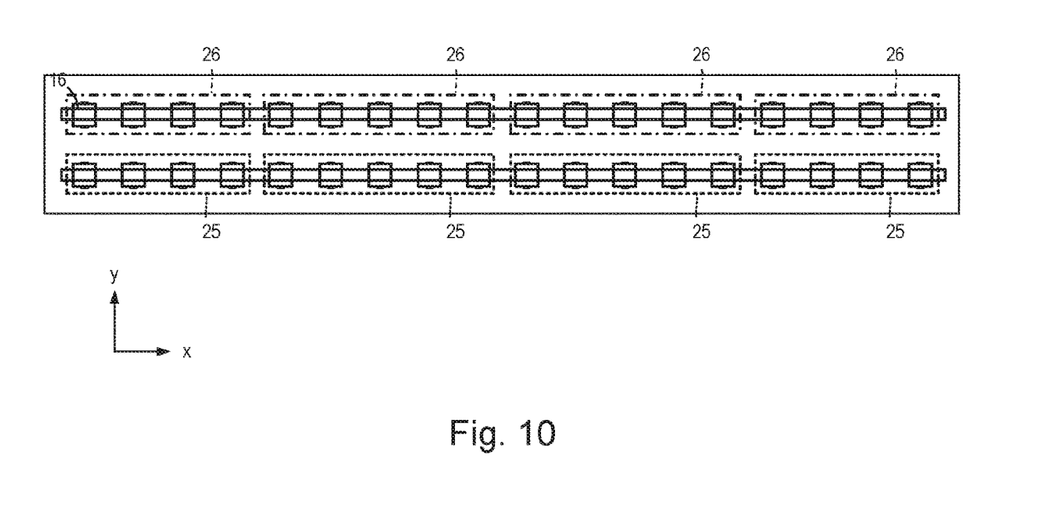
FIG. 10 is a plan view illustrating grouping of sensors into channels.

Referring in particular to FIG. 3, the ultrasonic sensor strip 1 includes a flexible circuit board 2 taking the form of a strip running between first and second ends 3, 4, along a longitudinal axis, and having first and second opposite side edges 5, 6. The flexible circuit board 2 comprises a substrate 7 formed from a dielectric material, such as polyimide or another suitable plastics material, having a surface 8 (herein referred to as an "upper surface") which supports conductive tracks 9 (FIG. 9). The substrate 7 has a thickness, s, which is preferably less than 2 mm or more preferably less than 1 mm.

The flexible circuit board 2 is sufficiently flexible that it can be elastically bent to have a sufficiently small radius of curvature to allow it be wrapped around or conform to a structure, such as a pipe having, for example, a 2-inch nominal bore or even 1-inch nominal bore. The flexible circuit board 2 need not take the form of rectangular strip. The flexible circuit board 2 can be a square, polygonal, or be multi-sided having a complex shape or be round, elliptical or arcuate.

Figure 4:
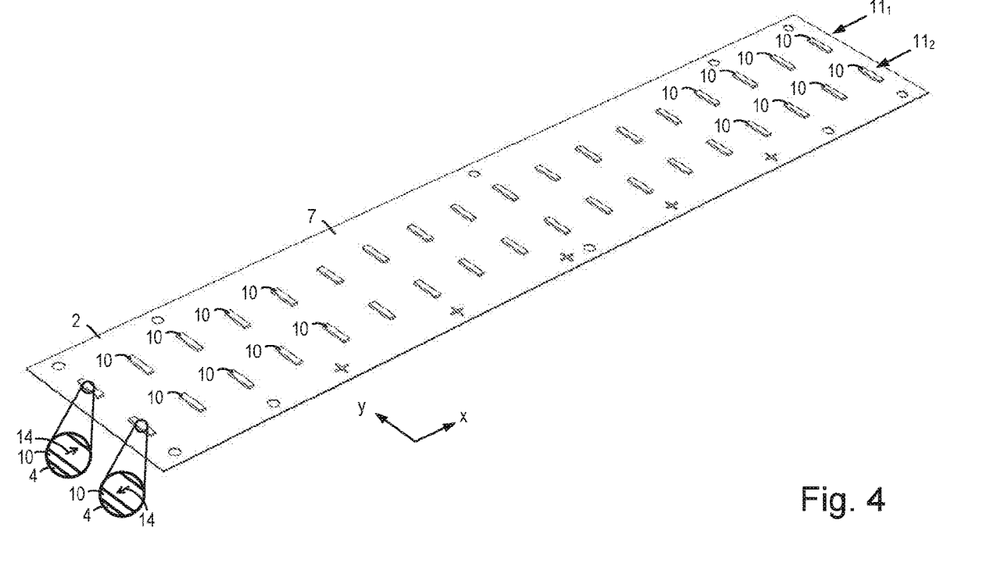
FIG. 4 is a perspective view of an assembly comprising a flexible circuit board supporting an array of piezoelectric transducers.
Figure 5:
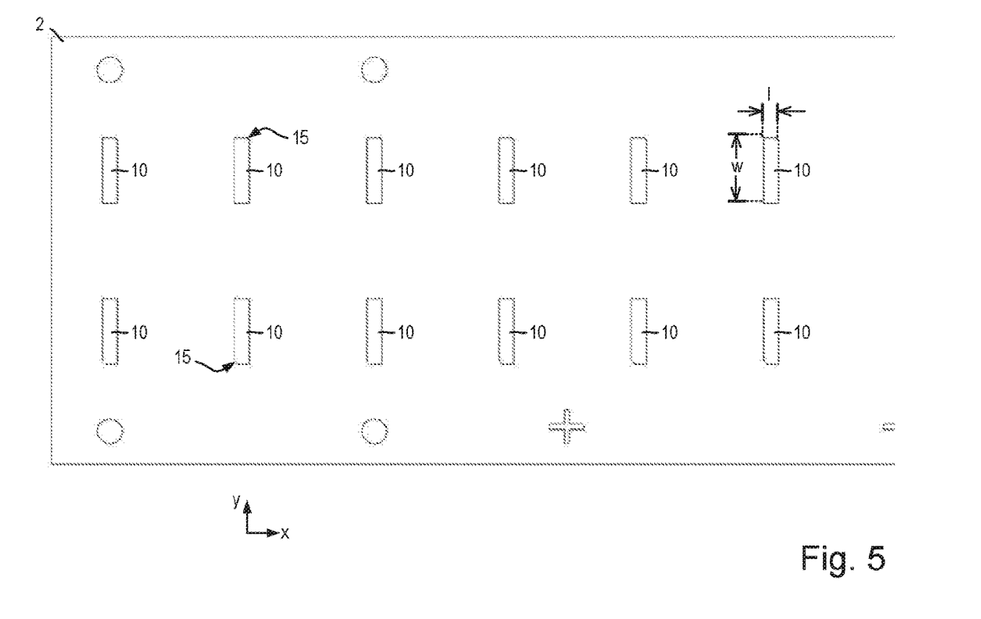
FIG. 5 is a magnified plan view of part of the assembly shown in FIG. 4.

Referring also to FIGS. 4 and 5, the flexible circuit board 2 supports an array of piezoelectric elements 10 arranged in two rows $11_1$, $11_2$ to form pairs $12_1$, $12_2$, $12_3$, ..., $12_n$ of piezoelectric elements 10 along the flexible circuit board 2. There may be only one row of piezoelectric elements 10 disposed on the board 2. There may be more than two rows of piezoelectric elements, for example, three, four, five or more rows, for example, nine rows disposed on the board 2. In this case, the array is a rectangular array. The piezoelectric elements 10 preferably comprise a block of lead zirconate titanate (PZT). The piezoelectric elements 10 are elongate, having a longitudinal axis and a polarization 14 arranged along its axis. In each pair $12_1$, $12_2$, $12_3$, ..., $12_n$, the piezoelectric elements 10 are orientated lengthwise across the strip-like board 2 and arranged end on with oppositely-orientated polarizations. The piezoelectric elements 10 may have polarizations orientated in the same direction. The piezoelectric elements 10 each have a chamfered corner 15 to help orientate them during assembly. The number and polarisation of piezoelectric elements depends on the modes to be excited in the structure.

Figure 6:
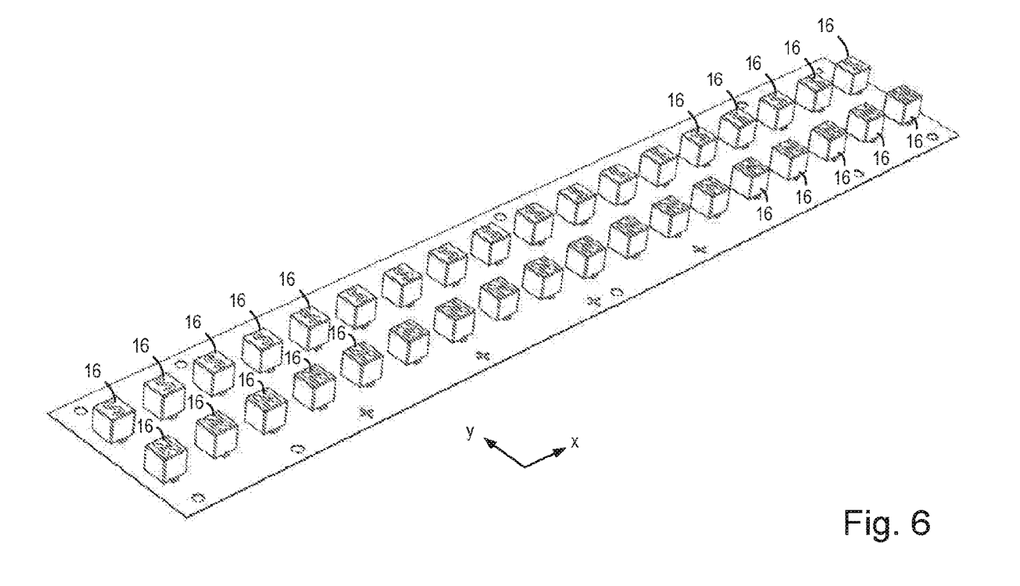
FIG. 6 is a perspective view of an assembly comprising a flexible circuit board supporting an array of piezoelectric transducers and an array of permanent magnets.

Referring also to FIG. 6, the sensor 1 includes an array of permanent magnets 16 also arranged in two rows $17_1$, $17_2$ to form pairs $18_1$, $18_2$, ..., $18_n$. The permanent magnets 16 may take the form of nickel-plated, neodymium iron boride (NdFeB) rare earth magnets. The permanent magnets can be made from other materials, such as ferrite or samarium cobalt. In this example, the permanent magnets 16 are cubes having dimensions 12 mm×12 mm×12 mm. However, the permanent magnets 16 need not be cubes and can have other dimensions. Each permanent magnet 16 sits over a respective piezoelectric element 10 such that each piezoelectric element 10 is interposed between a respective permanent magnet 16 and the flexible circuit board 2.

Figure 7:
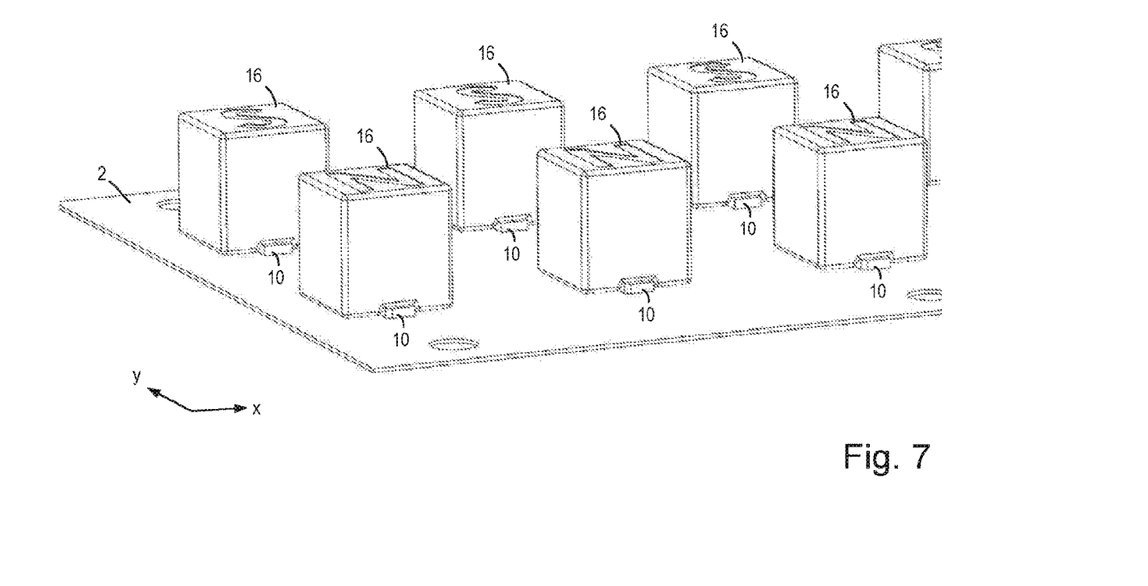
FIG. 7 is a magnified perspective view of part of the assembly shown in FIG. 6.

Referring also to FIG. 7, the permanent magnets 16 may have a groove 19 to help reduce the gap between the permanent magnets 16 and the pipe wall (not shown) and, thus, increase the magnetic force for pulling the piezoelectric elements 10 onto the pipe.

The permanent magnets 16 have respective magnetizations 20 which are orientated normally to the flexible circuit board 2. In one row $17_1$, the magnetizations 20 are arranged in one direction, for example, north pole up (with the south pole facing the flexible circuit board 2) and, on the other row $17_2$, the magnetizations 20 are arranged in the opposite direction, south pole up (with the north pole facing the strip). Thus, in each pair $18_1$, $18_2$, ..., $18_n$, the magnetisations 20 are oriented in antiparallel.

The permanent magnets 16 can be used to pull the strip 1 onto a steel pipe. Magnetic fields generated by the magnets 16 pass though the flexible circuit board 2 and pull the magnets 16 towards the wall of the pipe.

The piezoelectric elements 10 have a width (in the direction across the strip), w, of 13 mm, a length (in the direction along the strip), 1, of 3 mm and thickness, t, of 1 mm. The dimensions of the piezoelectric elements 10 may differ, i.e., larger or smaller elements may be used. The aspect ratio of the piezoelectric elements 10 may differ. The permanent magnets 16 have a transverse pitch (or "row-to-row spacing"), $p_1$, of 32 mm and a longitudinal pitch, $p_2$, of 26.25 mm. The first pitch and second pitch may vary. For example, the first pitch can be 21 mm (corresponding to a wavelength of 84 mm). Generally, the smaller the pipe diameter (and pipe wall thickness), a smaller pitch is used. Magnetization alternates between the rows, as opposed to going down the row, to help avoid the last permanent magnet $16_1$, $16_n$ (i.e., the magnets at start and the end of the row) being pulled towards the penultimate magnet $16_2$, $16_{(n-1)}$.

The piezoelectric elements 10 are preferably orientated so that they conform best to the curvature of the structure, e.g., pipe. In other words, the shorter sides (as opposed to the longer sides) of the piezoelectric elements 10 run along the strip and, thus, the circumference of the pipe.

Figure 8:
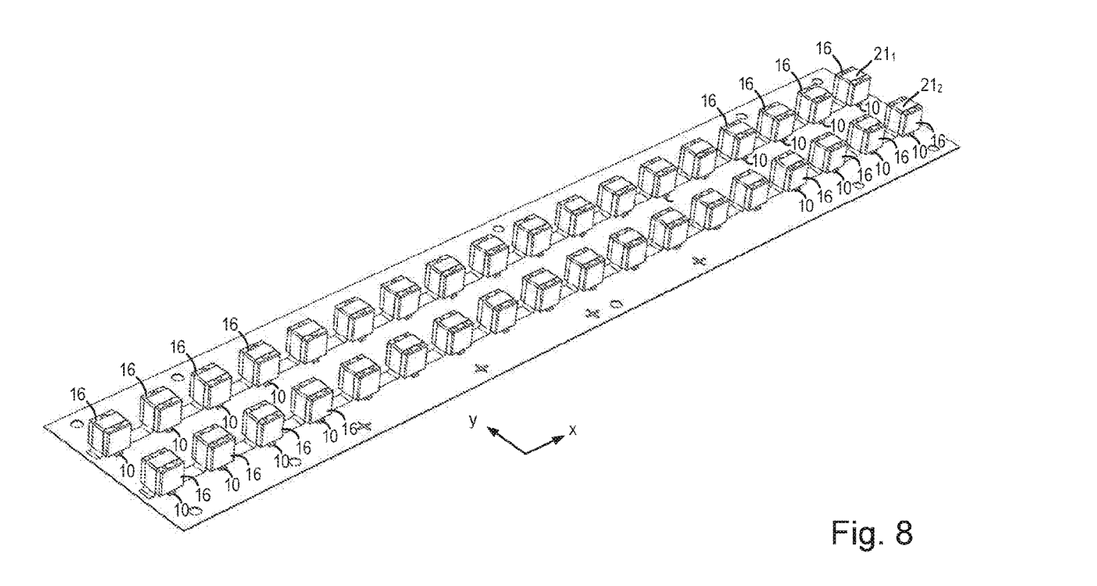
FIG. 8 is a perspective view of an assembly comprising a flexible circuit board supporting an array of piezoelectric transducers, an array of permanent magnets and conductive strips.

Referring also to FIG. 8, the sensor 1 includes first and second conductive strips $21_1$, $21_2$. The conductive strips $2_1$, $21_2$ are used for earthing and can be formed from copper or another suitable conductor. The first conductive strip $21_1$ runs along the flexible circuit board 2 over the first row $17_1$ of permanent magnets 16 and the second conductive strip $21_2$ runs along the flexible circuit board 2 in parallel to the first conductive strip over the second row $17_2$ of permanent magnets 16.

Referring also to FIG. 9, wires (not shown) are connected to the piezoelectric elements 10 via conductive tracks 9 of the flexible circuit board 2. The wires (not shown) are secured to the surface of the flexible circuit board 2 to help minimise the difference in radius of curvature between the flexible circuit board 2 and the wires (not shown) to avoid stressing the wires when the assembly is flexed. To provide further protection, the wires (not shown) may be follow a serpentine path and so avoid running straight along the path of the stress that results from wrapping a flat sensor around a pipe. The wires are omitted from the drawings for clarity.

The assembly of flexible circuit board 2, piezoelectric elements 10, wires (not shown), permanent magnets 17 and conductive strips $21_1$ , $21_2$ are encapsulated in an over-moulding 2223. The over-moulding 23 may comprise polyurethane. Other materials may be used, such as silicone or fluorosilicone. The over-moulding 23 includes a pipe portion 23 through which the wires (not show) emerge.

There is an ohmic electrical connection between the nickel plating on the permanent magnets 16 and the electrode (not shown) on the top of the piezoelectric element 10 in which can take the form of gold plating. This is used to provide an earth connection for the piezoelectric element 10. Using an appropriate jig (not shown), the permanent magnets 16 are bonded to the top of the piezoelectric element using non-conductive methacrylate adhesive or other suitable adhesive such as a conductive, metal-loaded, single part, heat cure epoxy resin. To provide electrical connections to the magnets 16, two strips of self-adhesive, nickel-plated copper are first adhered, then subsequently, soldered to each magnet 16 in the row, and the appropriate earth connections on the flexible circuit.

Referring also to FIG. 9, the piezoelectric elements 10 may be divided into groups to provide channels 25, 26. For example, FIG. 9 shows a two-row, eight-channel configuration with four channels per row.

For a small-diameter pipe, such as, for example, a "6-inch" nominal bore or 6.625-inch nominal outside diameter (168-centimetre), a single ultrasonic sensor strip 1 can be used as a transducer array ring. For a large-diameter pipe, such as, for example, a "24-inch" (61-centimetre) nominal bore, four ultrasonic sensor strips 1 can be combined to form a transducer array ring.

Referring in particular to FIG. 9, a channel 25 is shown. Conductive track(s) 9, for example formed from copper or other suitable material, on the flexible substrate 7 can be used to provide and collect signals with the piezoelectric elements 10. A single track 9 can be used to group elements 10 together.

To couple ultrasonic energy generated and received by the elements 10 into the wall of the pipe being tested, a shear couplant (not shown) may be used.

As the permanent magnets 16 have dimensions which can be similar to the thickness of the pipe under test, the permanent magnets 16 may have resonant modes which are similar to those of the pipe walls. To extract pipe wall thickness data from the transducer array, magnet resonances should be sufficiently damped so that they do not inject noise into the received signals around the frequencies of interest. Damping at frequencies of interest can vary according to the type of polyurethane used for overmoulding. A two-component polyurethane resin system can be used which behaves as an emulsion of both hard and soft elastomers and provide effective damping along with mechanical and environmental protection for the assembly.

Figure 11:
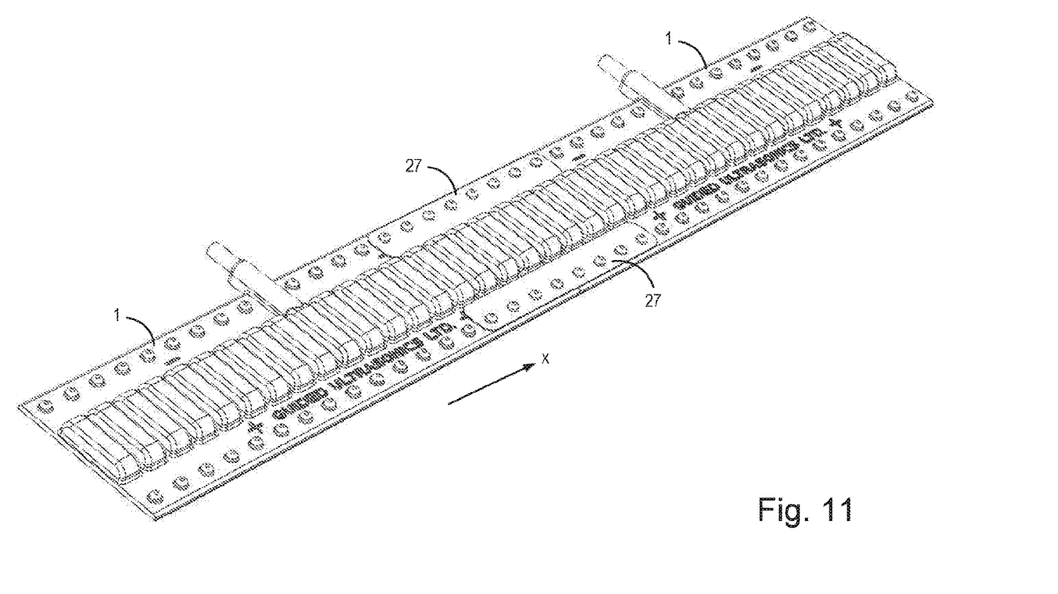
FIG. 11 is a perspective view of two sensors strip joined together using a patch.

Referring to FIG. 11, two or more ultrasonic sensors 1 can be attached to form longer or extended-area sensors using low-stretch joining strips 27, such as webbing (formed from, for example, Hypalon coated polyester), which run over flanking parts of the overmoulding of adjacent ultrasonic sensors 1 which are arranged end-to-end.

The ultrasonic sensor 1 can help the transducers 10 provide signals of generally equal signal strength. By holding the flexible circuit board 2 and the piezoelectric sensors 10 between the permanent magnets 16 and the pipe, the permanent magnets 16 bias the sensor strip 1 onto the wall of the pipe through magnetic attraction. The force that is applied to each piezoelectric element 10 is generated exclusively from a respective permanent magnet 16 behind the element 10 rather than, for example, hoop stress in a steel band which is used to urge the element onto the pipe. As the permanent magnets 16 are all the same size, material, and strength, and have the same offset from the pipe wall, then magnetic attraction forces should be equal for all piezoelectric elements 10. By normalising pressure on the piezoelectric elements 10, signals generated by the piezoelectric elements 10 should be equally matched. Having equal levels of force on all the transducers 10 should mean that the transmitted and received signals are all evenly matched, resulting in improved signal-to-noise ratios compared with unbalanced signals.

Because the flexible circuit board 2, piezoelectric elements 10, magnets 16 and earthing strips $21_1$, $21^2$ and wires (not shown) have no moving parts and are encapsulated in thick elastomer, the sensor sheet 1 can benefit from improved waterproofing. Moreover, because sensor 1 generally comprises a flat sheet with upstanding protrusions, the assembly conforms to a pipe surface by bending around the neutral axis of the flat sheet. The protrusions do not play a part in defining which parts of the assembly are in tension and those that are in compression. This means that the second moment of area of the elastomer that is being deformed around the pipe is very low, making it easy to use the same circuit on pipes having a diameter between 8 inches (20 centimetres) and 48 inches (122 centimetres) or more, or even a flat pate.

A transducer array ring (or simply "transducer ring") comprising a plurality of sensors 1 can be used in a number of different applications.

Figure 12:
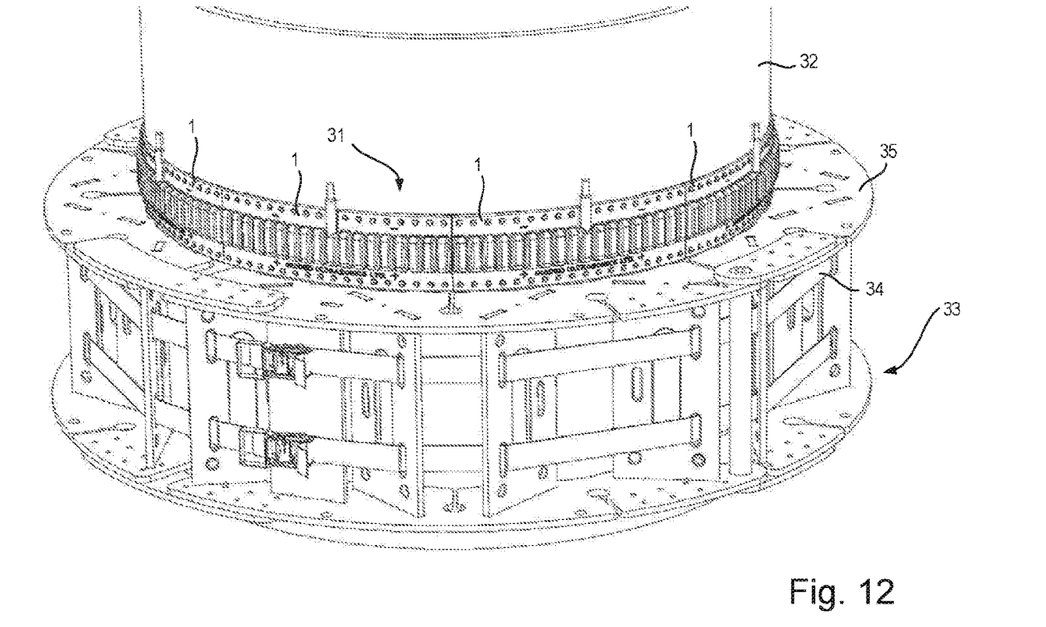
FIG. 12 is a perspective view of a plurality of sensors strips around a pipe and an alignment structure.
Figure 13:
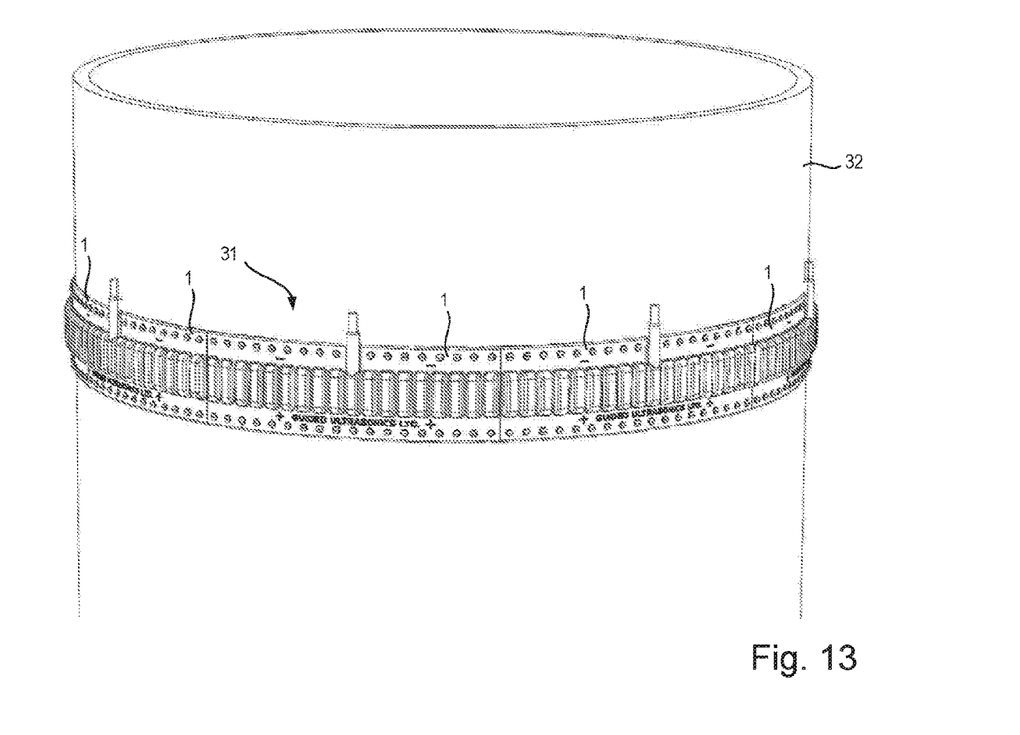
FIG. 13 is a perspective view of the plurality of sensors strips and pipe shown in FIG. 12 after the alignment structure has been removed.
Figure 14:
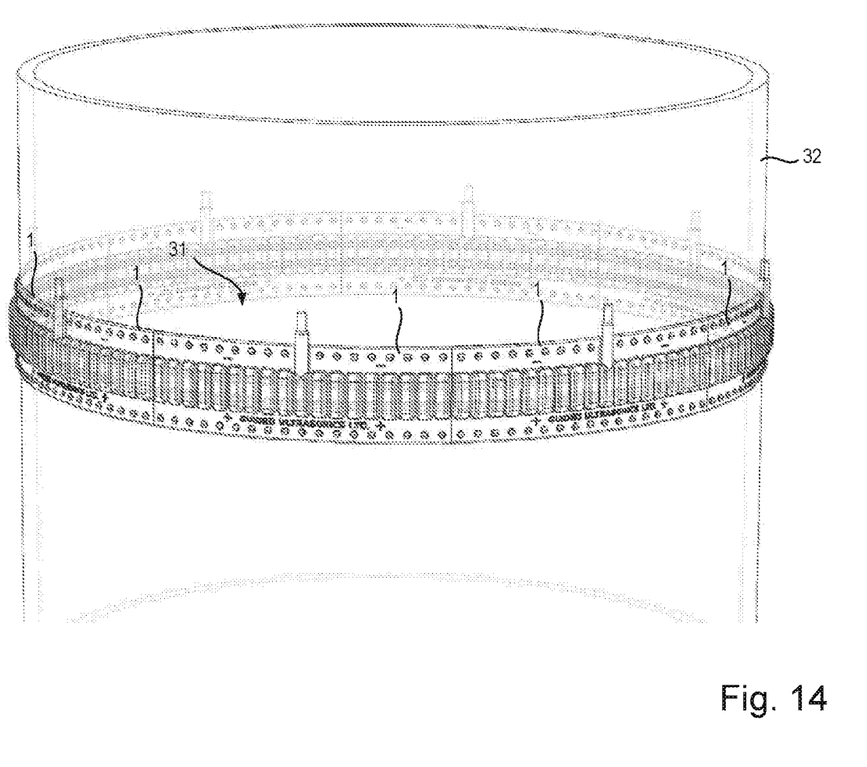
FIG. 14 is another perspective view of the sensor strips and pipe shown in FIG. 13 with the pipe shown semi-transparent for clarity.

Referring to FIGS. 12, 13 and 14, a removable, diver-installed subsea transducer array ring 31 is shown comprising a plurality of ultrasonic sensor 1.

After couplant is applied in the dry, the ring 31 is lowered down to a diver who installs the ring onto a pipe 32. An alignment aid 33 in the form of a shelf can be used to help align the ring 31 with the axis of the pipe 32. Ratchet straps 34 can be used to hold a support 35 in place. After testing, the ring 31 is removed and returned to top-side for cleaning and reapplication of couplant.

The ring 31 may be permanently installed. Instead of couplant, a waterproof epoxy resin, which is mixed and applied top side, then stuck onto the pipe subsea can be used.

The subsea transducer array ring 31 can be installed using a remotely operated underwater vehicle.

A transducer ring can be used in situations where is might be desirable to deploy a transducer ring quickly and the transducer ring is likely to get wet or where the transducer ring is deployed in swampy or shallow water conditions, such as, for example, in a splash zone on risers and river deltas. The transducer ring can be quick to install and quick to remove.

A transducer ring can be used internally, for example, inside wind turbine towers or inside drill pipe end inspections.

MODIFICATIONS

It will be appreciated that various modifications may be made to the embodiments hereinbefore described. Such modifications may involve equivalent and other features which are already known in the design, manufacture and use of ultrasonic sensors, particularly those for guided wave testing, and component parts thereof and which may be used instead of or in addition to features already described herein. Features of one embodiment may be replaced or supplemented by features of another embodiment.

The ultrasonic sensor(s) need not be arranged to form a closed ring. For example, sensor(s) can be applied as patches to pipes and plate-like structures.

The structure need not be a pipe, but can be another form of tubular structure, or even a rail.

Although claims have been formulated in this application to particular combinations of features, it should be understood that the scope of the disclosure of the present invention also includes any novel features or any novel combination of features disclosed herein either explicitly or implicitly or any generalization thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

The invention claimed is:

1. An ultrasonic sensor for guided wave testing comprising:
a flexible circuit board;
an array of piezoelectric elements on the flexible circuit board; and
an array of permanent magnets, each piezoelectric element interposed between a respective permanent magnet and the flexible circuit board, wherein each permanent magnet has a notch for accommodating a respective piezoelectric element for reducing a gap between each respective permanent magnet and the flexible circuit board.

2. The ultrasonic sensor of claim 1, wherein the piezoelectric elements are shear-polarized piezoelectric elements.

3. The ultrasonic sensor of claim 1, wherein the piezoelectric elements are arranged in first and second rows in a first direction across the flexible circuit board, wherein polarization of the piezoelectric elements in the first row are in the same direction.

4. The ultrasonic sensor of claim 3, wherein polarization of the piezoelectric elements in the first row and polarization of the piezoelectric elements in the second row are the same.

5. The ultrasonic sensor of claim 3, wherein the polarization of the piezoelectric elements in the first row and the polarization of the piezoelectric elements in the second row are antiparallel.

6. The ultrasonic sensor of claim 1, wherein the array of piezoelectric elements comprises between 10 and 500 piezoelectric elements.

7. The ultrasonic sensor of claim 1, wherein the piezoelectric elements comprise a block of lead zirconate titanate.

8. The ultrasonic sensor of claim 1, wherein the permanent magnets comprise a rare earth metal or ferrite.

9. The ultrasonic sensor of claim 1, further comprising:
at least one conductive strip running over a line of permanent magnets and on the flexible circuit board between the permanent magnets along the flexible circuit board.

10. The ultrasonic sensor of claim 9, wherein the at least one conductive strip comprises at least one metallic strip.

11. The ultrasonic sensor of claim 1, further comprising:
a set of wires, wherein each wire is connected to a respective conductive track of the flexible circuit board and the conductive track is connected to a respective piezoelectric element or to a respective set of two or more piezoelectric elements.

12. The ultrasonic sensor of claim 1, further comprising:
an overmould encapsulating at least the flexible circuit board, the piezoelectric elements, and the permanent magnets.

13. A transducer array ring comprising:
a plurality of ultrasonic sensors, each of the plurality of sensors respectively comprising:
a flexible circuit board;
an array of piezoelectric elements on the flexible circuit board; and
an array of permanent magnets, each piezoelectric element interposed between a respective permanent magnet and the flexible circuit board, wherein each permanent magnet has a notch for accommodating a respective piezoelectric element for reducing a gap between each respective permanent magnet and the flexible circuit board.

14. The transducer array ring according to claim 13, further comprising:
first and second joining strips arranged to overlap first and second ultrasonic sensors arranged end-to-end or side-by-side and secured to the first and second ultrasonic sensors.

15. A method, comprising:
  installing by attaching an ultrasonic sensor or transducer array ring to an inner wall of a ferromagnetic structure, wherein the transducer array ring comprises a plurality of ultrasonic sensors, the sensor or each of the plurality of sensors comprising:
  a flexible circuit board;
  an array of piezoelectric elements on the flexible circuit board;
  an array of permanent magnets, each piezoelectric element interposed between a permanent magnet and the flexible circuit board.

16. The method of claim 15, wherein the ultrasonic sensor or transducer array ring is secured to the ferromagnetic structure without an adhesive or a retaining band.

17. The method of claim 15, further comprising:
  removing the ultrasonic sensor or transducer array ring from the ferromagnetic structure.

18. The method of claim 15, further comprising:
  using the ultrasonic sensor or transducer array ring in or in the vicinity of water.

* * * * *